United States Patent [19]
Abate

[11] Patent Number: 5,510,117
[45] Date of Patent: Apr. 23, 1996

[54] ENTRAPMENT VEHICLE AND METHOD

[75] Inventor: Kenneth Abate, Amherst, N.H.

[73] Assignee: Micro-Pak, Inc., Wilmington, Del.

[21] Appl. No.: 335,207

[22] Filed: Nov. 7, 1994

Related U.S. Application Data

[63] Continuation of Ser. No. 964,418, Oct. 21, 1992, abandoned, which is a continuation-in-part of Ser. No. 759,239, Sep. 13, 1991, abandoned, which is a continuation of Ser. No. 490,356, Mar. 8, 1990, Pat. No. 4,952,550, which is a continuation-in-part of Ser. No. 320,944, Mar. 9, 1989, Pat. No. 4,959,341.

[51] Int. Cl.$^6$ .............................. A61K 9/14; B01J 13/02
[52] U.S. Cl. ........................ 424/489; 424/490; 424/493; 424/494; 424/496; 424/497; 424/499; 424/500; 424/501; 428/402.2; 264/41; 264/43
[58] Field of Search ..................... 424/489–501; 428/402.2; 264/4.1, 4.3; 514/937–943

[56] References Cited

U.S. PATENT DOCUMENTS

| | | | |
|---|---|---|---|
| 3,549,555 | 10/1970 | Hiestand | 424/494 |
| 3,860,490 | 1/1975 | Guttag | 195/108 |
| 3,875,074 | 4/1975 | Vassiliades | 424/494 |
| 3,956,172 | 5/1976 | Saeki | 252/316 |
| 3,969,280 | 7/1976 | Sayce | 252/522 |
| 4,010,038 | 3/1977 | Iwasaki | 106/22 |
| 4,090,013 | 5/1978 | Gamslaw | 526/15 |
| 4,247,411 | 1/1981 | Vanlerberghe et al. | 252/316 |
| 4,251,387 | 2/1981 | Lim et al. | 252/316 |
| 4,402,856 | 9/1983 | Schnoring | 428/402.22 |
| 4,690,682 | 9/1987 | Lim | 604/891 |
| 4,911,928 | 3/1990 | Wallach | 424/450 |
| 4,952,550 | 8/1990 | Wallach et al. | 502/404 |
| 4,959,341 | 9/1990 | Wallach | 502/404 |
| 4,996,150 | 2/1991 | Joung | 435/161 |
| 5,019,392 | 5/1991 | Wallach | 424/420 |

Primary Examiner—Gollamudi S. Kishore

[57] ABSTRACT

This invention concerns delivery vehicles entrapping active materials suspended in a water immiscible carrier. Methods of making these materials, preferably using a carboxymethylcellulose support martrix, are disclosed. The vehicles of the invention are especially well adapted to delivery of incompatible actives that can be entrapped separately and kept separately until release from the vehicle.

14 Claims, No Drawings

ENTRAPMENT VEHICLE AND METHOD

REFERENCED RELATED APPLICATIONS

This application is a continuation of application Ser. No. 07/964,418, filed on Oct. 21, 1992, now abandoned, which is a continuation-in-part of U.S. patent application Ser. No. 759,239, filed Sep. 13, 1991, now abandoned, which is a continuation of Ser. No. 07/490,356, filed Mar. 8, 1990, now U.S. Pat. No. 4,952,550, issued Aug. 28, 1990, which itself is a continuation-in-part of Ser. No. 07/320,944, filed Mar. 9, 1989, now U.S. Pat. No. 4,959,341, issued Sep. 25, 1990. The disclosures of each of the above-referenced applications are incorporated herein by reference.

BACKGROUND OF THE INVENTION

The present invention relates to delivery vehicles having active materials entrapped therein. These delivery vehicles are suspended in water immiscible carriers. The present invention allows two incompatible active substances to be delivered together without cross-reactivity so that they keep their full activity until the delivery vehicle is destroyed or the materials leach from the vehicles.

A number of different delivery vehicles have been developed for entrapment of materials. These delivery vehicles include microcapsules, liposomes, other types of lipid vesicles, cellulosic materials and polymer delivery systems. These vehicles are used primarily to carry aqueous solutions of active materials. U.S. Pat. No. 4,911,928, the disclosure which is incorporated herein by reference, is one of the few patents that concerns the entrapment of material in a water immiscible liquid, not an aqueous solution. This patent discloses the making of paucilamellar lipid vesicles which have an amorphous central cavity that can be filled with a water immiscible material such as an oil. The water immiscible material acts as a carrier for a material which is soluble or suspendable in that oil. The oil is carried in the central cavity, not the external phase.

However, for certain uses, even the lipid vesicles described in the aforementioned patent can leak or break down so that cannot be used. This can be disastrous if the encapsulated materials are incompatible. One attempt to achieve the desired results was using a vesicle incorporating a water immiscible material entrapping a water immiscible active and have another active in an external phase. This type of procedure is described in U.S. Pat. No. 5,019,392, the disclosure which is incorporated herein by reference. However, this method also cannot be used for certain materials. One problem is that for stability reasons, the vesicles often work best if there is an external aqueous phase. Similarly, although blends of lipid vesicles carrying two different materials are known (see, e.g., U.S. Pat. No. 4,247,411), these vesicles have not been used for non-aqueous materials (which fall out side the scope of the '411 patent) and these vesicles are only described as being suspended in an external aqueous solution.

Similarly, most microcapsule work has aqueous solutions both as the entrapped material filling the central cavity and as the external phase. Microcapsules are often made by reacting the monomers forming the polymer at an interface or by cross-linking a material such as an alginic acid derivative with a divalent metal ion. If the alginic acid procedure is used, the cross-linked material is formed into a capsule membrane by reaction with a second polymer. U.S. Pat. No. 4,690,682 describes such a procedure.

In interfacial polymerization, the material to be encapsulated and a hydrophilic monomer is emulsified within a hydrophobic continuous phase and a second monomer is then dissolved in the continuous phase. Polymerization occurs at the boundary between the two phases where the two monomers can interact to form the polymeric material. U.S. Pat. No. 4,251,387 discloses this type of technique. By modifying the conditions of reaction, improved microcapsule membranes can be formed.

Still another entrapment technique is shown in U.S. Pat. No. 3,860,490. In this patent, a microorganism is mixed with acrylate and methacrylate monomers and polymerization is allowed to occur to form a gel lattice about the microorganism. After separation, an additional coating of the polymer may be formed about the entrapped material. In one aspect of this patent, a particulate material is used as a carrier to which the microorganisms are absorbed and then the polymeric coating is formed by a polymerization reaction about the particulate.

While all of the foregoing techniques have substantial uses, in certain instances, particularly where the active material to be entrapped is not soluble or dispersible in aqueous solutions, these techniques may not be appropriate. Further, leaching of the active through pores of the microcapsules or liposomes can be a problem in certain circumstances. In addition, some of these vesicular structures or microcapsules are not stable if a water immiscible carrier is used as the external phase.

Accordingly, an object of the invention is to provide a method of making a delivery vehicle which can be suspended in a water immiscible carrier without leaching of the active.

A further object of the invention is to provide a method of entrapping two incompatible materials while preventing them to cross-react.

Another object of the invention is to provide a delivery system for delivering two incompatible materials in a water immiscible carrier.

These and other objects and features of the invention will be apparent for the following description and the claims.

SUMMARY OF THE INVENTION

The present invention features a method of preparing a delivery vehicle having an entrapped active substance therein, a method of delivering two incompatible materials, and a system for delivering the two incompatible materials. The active materials to be delivered are entrapped within a cross-linked particulate material which is then suspended in a water immiscible carrier.

The method of preparing a delivery vehicle having an entrapped active material has the initial step of suspending a particulate support material in an aqueous material solution containing the active material to be entrapped. The term "suspended" or "suspension", as used herein, means not just classical suspensions but also colloids, emulsions, and other forms of keeping the material in a non-precipitated, non-dissolved form. The term "contained" means not just dissolved but also suspended, carried in the form of a colloid carrier, carried as part of an emulsion, or otherwise carried in non-precipitated form. If a material is dissolved in a phase, it is deemed "contained", not "suspended".

The support material is selected from the group consisting of carboxylated cellulosic materials, chitosan, guar gum, alginic acid and its salts, polymethacrylates, polyacrylates, and copolymers and mixtures thereof. The support material does not dissolve in the aqueous solution and preferrably does not include monomers used to make a polymeric material.

The support material suspension is blended with a water immiscible carrier to form a suspension of the support material in the water immiscible carrier. A cross-linking agent, which is insoluble in the aqueous solution but soluble in the water immiscible carrier, is added and allowed to react with and cross-link the support material, thereby forming the delivery vehicle. This final delivery vehicle has the active material entrapped in cross-linked support material which is suspended in the water immiscible carrier.

The preferred cross-linking agents are metallo-organic complexes, particularly complexes of carboxylic acids or their active derivatives with divalent or multivalent metal ions. The term "active derivatives" as used herein includes salts, amines, amides, ethers, esters, alkoxides, and carbanyls of the carboxylic acids. The preferred carboxylic acids are high molecular weight carboxylic acids or branched carboxylic acids because of their insolubility in water. The most preferred cross-linking agent is a primary or secondary aluminum or chromium alkoxide, most preferably aluminum isopropoxide. The preferred support material is a carboxylated cellulosic material, specifically carboxymethylcellulose ("CMC"), most preferable CMC having a DS (or degree of substitution) of 0.5 or greater. While any water immiscible carrier could be used, oils, triglycerides, waxes and ethers which are flowable at the cross-linking conditions are preferred. Most preferred oils include mineral oil, soybean oil, castor oil and their mixtures. The aqueous solution could be plain water but preferably is an electrolyte solution such as a saline solution and may include a pH modifier such as an acid, particularly a carboxylic acid or a base. The most preferred aqueous solution is a saline/acetic acid solution.

The main requirement for the active ingredient useful in the invention is that it can be contained in the aqueous phase. Preferred active materials include levamisole, closantel, pyrethrins, pyrethroids, carbamates, water-insoluble organo-phosphorous compounds, benzoyl urea, triazines, avermectins, and milbemycins and other water insoluble ectoparasiticides and endoparasiticides. However, any active that can be contained in aqueous solution but is not soluble in the selected water immiscible carrier can be used.

In addition, the water immiscible carrier may include a stabilization agent such as a nonionic or anionic surfactant. While this stabilization agent is not necessary, it can assist in forming stable oil-in-water emulsions prior to cross-linking. A sorbitan derivative is preferred as a stabilization agent, but other surfactants could be used.

In one aspect of the invention, two incompatible active materials can be used to form a combination product which would not otherwise be stable. A first delivery vehicle is formed by entrapping one of the incompatible materials using the procedure prescribed previously. A second delivery vehicle is then formed to entrap the second of the incompatible materials, again using the same procedure. Different materials can be used as the particulate support material, the carrier, the aqueous solution, and the other reactants so long as the water immiscible carriers are compatible with the support materials and each other. The two delivery vehicles are blended and suspended in a common water immiscible carrier to form the combination product. The incompatible materials cannot react until they are released from the cross-linked support material, something that will normally happen only by degradation or other breakdown. For example, ecto- and endoparasiticides can be delivered simultaneously. If ectoparasiticides are used as one of the materials, preferred ectoparasiticides include the group consisting of pyrethrins, pyrethroids, carbamates, water-insoluble organo-phosphorous compounds, benzoyl urea, triazines, avermectins, and milbemycins. If endoparasiticides are used, the thiazoles are preferred.

Still another aspect of the invention, concerns the delivery vehicle itself for delivering these two incompatible materials. This delivery of vehicle is a combination of a first delivery vehicle and a second delivery vehicle, each of the delivery vehicles being an acid-stablized cross-linked carboxymethylcellulose in a water immiscible carrier. These two delivery vesicles are blended to form the delivery system of the invention. Each of these delivery vehicles can be made using the methods and materials previously described.

Other features of the invention will be apparent from the following description.

DETAILED DESCRIPTION OF THE INVENTION

The present invention concerns a method of entrapping an active material in a particulate support material which is itself suspended in a water-immiscible material such as an oil. This invention is particularly advantageous where two incompatible active materials are to be used. Each active can be entrapped separately and then a blend is made of the entrapped actives in the water immiscible material. If the actives are not soluble in the water immiscible material, the actives cannot leach from the carriers. Since each of these entrapped actives is kept separate from the other, no cross-reactivity or other interaction can occur. While this is particularly advantageous if the two actives are incompatible, it also could be used where the actives, although compatible, are to be kept separate until they are removed from the water immiscible material. For example, it might be possible to have two monomers of a polymeric material, delivered to the same location, and only upon removal of the external water immiscible material or breakdown of the support materials can they interact to form the polymer.

While the present invention can be used for aqueous soluble materials, it is particularly advantageous if the active to be entrapped is dispersible, but not soluble, in aqueous solutions. In this circumstance, the active is kept dispersed with the particulate support material until entrapped by the addition of the cross-linking agent. Cross-linking agents for this procedure are soluble in the external phase, the water immiscible carrier, but not in the aqueous phase. Aggregate size can be controlled by modifying the emulsion conditions and the cross-linking takes place only at the boundary of the phases. In contrast, many prior entrapping vehicles require that the active be aqueous soluble, not dispersible.

The following example will more clearly illustrate the efficacy of the invention. The example is merely illustrative and should not be deemed limiting in any way.

EXAMPLE

In this example, levamisole and closantel, which are incompatible anthelmintics used for animal treatment, were entrapped in a single two-component system. This system is particularly well adapted for use in animals such as sheep.

Levamisole, in the form of levamisole-HCl, is water soluble, while closantel-Na is not soluble but rather is dispersible in aqueous solutions. These materials react if brought in contact, losing the efficacy of both. The levamisole and closantel are available from Janssen Pharmaceutica NV.

Vehicles entrapping these materials are made as follows. Three stock solutions for use in making both vehicles are prepared first: Solution A has 175.8 ml of soybean oil with 1.87 g of SPAN 60 (sorbitan monostearate) dissolved therein by heating the solution for approximately 50° C. until it becomes clear. This water immiscible carrier solution is approximately 1% by weight SPAN 60, which acts as a stabilizer.

Solution B is 10% acetic acid in water. About 0.625 ml is used in making each vehicle.

Solution C is a 10% MANALOX 130 (Rhone Poulenc) solution in soybean oil. MANALOX 130 is itself a 10% solution of aluminum isopropoxide, yielding a final concentration of 1% aluminum isopropoxide in soybean oil. About 12.5 ml of Solution C is used in making each vehicle.

The solutions of the two active materials are made as follows:

Solution D is 50 ml of a 1% carboxymethylcellulose (9H4F from Aqualon Company) in normal saline (approximately 0.9% weight) to which 18.75 g of levamisole-HCl is added. Solution E is identical to Solution D except 25 g of closantel-Na is added instead of the levamisole.

Two different procedures can be used which yield substantially the same results. In the first procedure, Solution D or E is added to Solution A, under agitation sufficient for dispersion into small particles, followed by the dropwise addition of Solution B. The preferred procedure has Solution B added dropwise to Solution A before the addition of Solution D or E. The combined solutions are homogenized by an overhead stirrer or a magnetic stirrer for at least five minutes, then Solution C, the cross-linking agent, is added drop-wise while stirring and homogenizing. The stirring and homogenizing is continued at approximately 7,500 RPM for an additional 20 minutes.

Each of the two vehicles (those containing the levamisole and the closantel) are made separately. These vehicles in soybean oil may be kept separate or a combined product may be made by mixing equal amounts of the two materials. The combination product will contain approximately 37.5 mg/ml of levamisole-HCl and 50 mg/ml closantel-Na.

The foregoing example has also been tested with different amounts of each active, additional concentrations of CMC, different cross-linking agents and different dispersion methods. Substantially the same results have been obtained in all of these procedures.

The following claims more clearly define the invention. Those skilled in the art may discover other examples which are equivalent to those shown herein. Such other examples and procedures and encompassed within the following claims.

What is claimed is:

1. A method of preparing a delivery vehicle having an active material entrapped therein, said delivery vehicle being suspended in a water immiscible carrier, said method consisting essentially of the steps of:

suspending a particulate support material in an aqueous solution containing the active material to be entrapped, said support material being selected from the group consisting of crosslinkable carboxylated celluloses, chitosan, guar gum, polymethacrylates, polyacrylates, and mixtures thereof;

blending said support material suspension with a water-immiscible carrier to form a suspension of said support material in said water-immiscible carrier, said active material being insoluble in said water-immiscible carrier;

adding a cross linking agent to said water-mmiscible carrier, said cross-linking agent being insoluble in said aqueous solution but soluble in said water-immiscible carrier; and allowing said cross-linking agent to cross-link said support material, said cross-linking occurring at the phase boundary, thereby forming said delivery vehicle;

whereby said delivery vehicle is in the form of a cross-linked support material having said aqueous solution containing the active material entrapped therein, said delivery vehicle being suspended in said water-immiscible carrier.

2. The method of claim 1 wherein said cross-linking agent is a metallo-organic complex selected from the group consisting of complexes of divalent or multivalent metal ions with carboxylic acids and complexes of divalent or multivalent metal ions with salts, amines, amides, ethers, esters, alkoxides and carbonyls of carboxylic acids, said complex being insoluble in said aqueous solution and soluble in said water-immiscible carrier.

3. The method of claim 1 wherein said cross-linking agent is selected from the group consisting of primary aluminum alkoxides, secondary aluminum alkoxides primary chromium alkoxides, secondary chromium alkoxides, and mixtures thereof.

4. The method of claim 3 wherein said alkoxide comprise aluminum isopropoxide.

5. The method of claim 1 wherein said carboxylated cellulose is carboxymethylcellulose.

6. The method of claim 5 wherein said carboxymethylcellulose has a DS of 0.5 or greater.

7. The method of claim 1 wherein said water immiscible carrier is flowable under the cross-linking conditions, said water immiscible carrier being selected from the group consisting of oils, triglycerides, waxes, and ethers.

8. The method of claim 7 wherein said oil is selected from the group consisting of mineral oil, soybean oil, castor oil and mixtures thereof.

9. The method of claim 1 wherein said aqueous solution comprises an electrolyte solution.

10. The method of claim 9 wherein said electrolyte solution comprises a saline solution.

11. The method of claim 10 wherein said electrolyte solution further comprises a carboxylic acid.

12. The method of claim 11 wherein said carboxylic acid comprises acetic acid.

13. The method of claim 1 wherein said active material is selected from the group consisting of levamisole, closantel, pyrethrins, pyrethroids, carbamates, water-insoluble organophosphorous compounds, benzoyl urea, triazines, avermectines, and milbemycins.

14. The method of claim 1 wherein said water-immiscible carrier further comprises a stabilization agent selected from the group consisting of a non-ionic and anionic surfactants.

* * * * *